(12) United States Patent
Wei et al.

(10) Patent No.: US 11,332,433 B2
(45) Date of Patent: May 17, 2022

(54) PROCESS FOR THE PREPARATION OF LATANOPROSTENE BUNOD AND INTERMEDIATE THEREOF AND COMPOSITIONS COMPRISING THE SAME

(71) Applicant: CHIROGATE INTERNATIONAL INC., Yangmei (TW)

(72) Inventors: Shih-Yi Wei, Yangmei (TW); Ming-Kun Hsu, Yangmei (TW); Tzyh-Mann Wei, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 16/938,238

(22) Filed: Jul. 24, 2020

(65) Prior Publication Data

US 2022/0024849 A1   Jan. 27, 2022

(51) Int. Cl.
*C07C 201/02*   (2006.01)
*C07C 203/04*   (2006.01)
*C07C 69/732*   (2006.01)
*C07F 7/02*   (2006.01)
*A61K 31/216*   (2006.01)

(52) U.S. Cl.
CPC .......... *C07C 201/02* (2013.01); *C07C 69/732* (2013.01); *C07F 7/025* (2013.01); *A61K 31/216* (2013.01); *C07C 203/04* (2013.01)

(58) Field of Classification Search
None
See application file for complete search history.

(56) References Cited

U.S. PATENT DOCUMENTS 9,994,543 B2    6/2018  Wei et al.
2005/0272743 A1*  12/2005  Ongini ............... A61P 27/06
                                                 514/255.01

FOREIGN PATENT DOCUMENTS

WO   2005/068421 A1   7/2005
WO   2017/093771 A1   6/2017
WO   2019/031774 A1   2/2019

* cited by examiner

*Primary Examiner* — Amy C Bonaparte
(74) *Attorney, Agent, or Firm* — Ladas & Parry LLP

(57) ABSTRACT

Processes for preparing latanoprostene bunod and an intermediate prepared from the process. Also latanoprostene bunod compositions having high-purity latanoprostene bunod.

3 Claims, No Drawings

PROCESS FOR THE PREPARATION OF LATANOPROSTENE BUNOD AND INTERMEDIATE THEREOF AND COMPOSITIONS COMPRISING THE SAME

FIELD OF THE INVENTION

The present invention relates to processes for the preparation of latanoprostene bunod and an intermediate thereof, and compositions comprising the same.

BACKGROUND OF THE INVENTION

Latanoprostene bunod of Formula I is an active pharmaceutical ingredient (API) of Vyzulta, an ophthalmic solution for open-angle glaucoma or ocular hypertension:

WO 2005/068421 and WO 2017/093771 both disclose processes for preparing latanoprostene bunod by reacting latanoprost acid with 4-bromobutyl nitrate, as shown in Scheme 1. However, various impurities including isomers from latanoprost acid and by-products, such as Compound LB-Br and Compound LB-I, will be generated during the processes:

WO 2019/031774 discloses a process for preparing latanoprostene bunod by reacting AgNO$_3$ and Compound LB-Br prepared from latanoprost acid and 1,4-dibromobutane, as shown in Scheme 2:

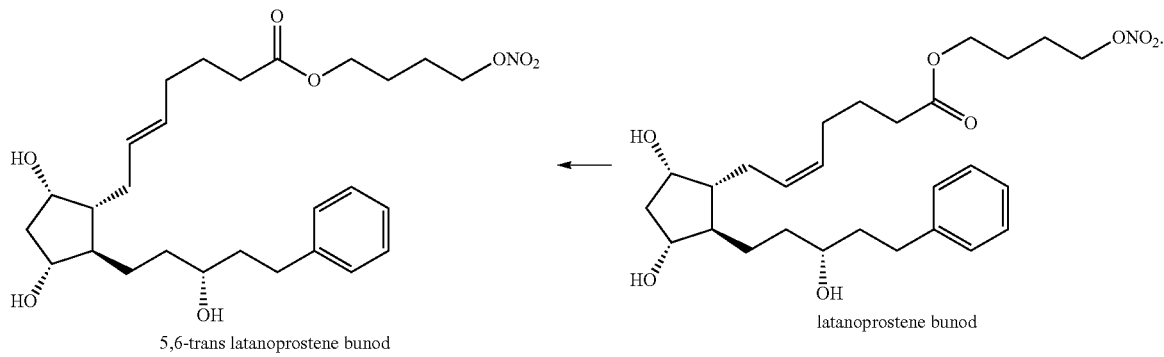

5,6-trans latanoprostene bunod latanoprostene bunod

However, there always exists a certain amount of unreacted Compound LB-Br in the reaction of LB-Br with AgNO$_3$, even if the reaction is carried out at high temperature for a long time. Moreover, 5,6-trans latanoprostene bunod will also be generated by isomerization of latanoprostene bunod during the high-temperature, long-term reaction. Thus, the process of WO 2019/031774 not only has the problems of impurity Compound LB-Br, but also 5,6-trans latanoprostene bunod.

Since latanoprostene bunod is in an oil form, its impurities cannot be removed by crystallization purification, but might be removed by chromatography. Nevertheless, due to the polarity of Compound LB-Br and Compound LB-I being very similar to that of latanoprostene bunod (TLC ΔRf<0.1), and the polarity of 5,6-trans latanoprostene bunod being almost the same as that of latanoprostene bunod, it is still very difficult to remove impurity Compound LB-Br, Compound LB-I and 5,6-trans latanoprostene bunod from latanoprostene bunod by chromatography, and even if it is possible, the cost would be very high.

WO 2017/093771 discloses the use of gravity silica gel column chromatography with a large amount (100-fold amount) of specific silica gel to purify crude latanoprostene bunod. After purification, 5,6-trans latanoprostene bunod and other by-products can be partially removed. However, in order to reduce the high cost of purification in the industry, it is better to avoid or reduce the generation of impurities, such as Compound LB-Br, Compound LB-I, and 5,6-trans latanoprostene bunod, which are difficult to be removed or separated during the preparation of latanoprostene bunod.

SUMMARY OF THE INVENTION

In one aspect, the present invention provides an efficient and economical process for the preparation of latanoprostene bunod without generating the aforementioned Compound LB-Br or Compound LB-I and with minimized 5,6-trans latanoprostene bunod, which are difficult to be removed or separated.

An embodiment of the present invention relates to a novel process for preparing latanoprostene bunod, which comprises the step of reacting latanoprost acid with 1,4-butanediol dinitrate.

An embodiment of the present invention relates to a process for purification of crude latanoprostene bunod by silylating all the hydroxyl groups in the crude latanoprostene bunod with a silylating agent comprising the residue —SiR$_a$R$_b$R$_c$, to form a compound of Formula LB-3Si,

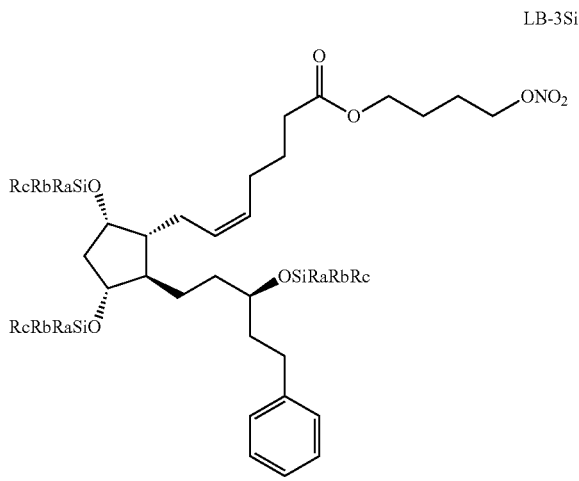

LB-3Si wherein R$_a$, R$_b$ and R$_c$ are each independently C$_{1-8}$ alkyl, phenyl, benzyl, a substituted phenyl, or a substituted benzyl; and then desilylating the resultant compound of Formula LB-3Si, to form latanoprostene bunod, which has higher purity than the crude latanoprostene bunod.

In one aspect, the present invention provides a novel intermediate of Formula LB-3Si as defined above.

In another aspect, the present invention provides a process comprising esterifying latanoprost acid with 1,4-butanediol dinitrate to form latanoprostene bunod and a compound of Formula LB-dimer, LB-dimer

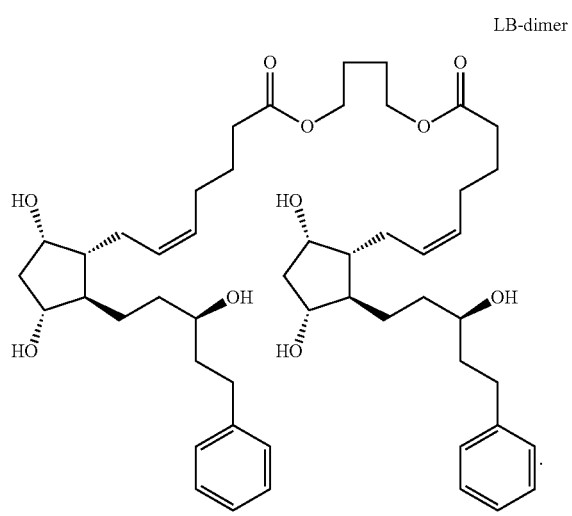 [SMILES: O=C(CCC/C=C\C[C@@H]1[C@@H](CC[C@@H](O)CCc2ccccc2)[C@H](O)C[C@@H]1O)OCCCCOC(=O)CCC/C=C\C[C@@H]1[C@@H](CC[C@@H](O)CCc2ccccc2)[C@H](O)C[C@@H]1O]

In another aspect, the present invention provides a novel compound of Formula LB-dimer, LB-dimer

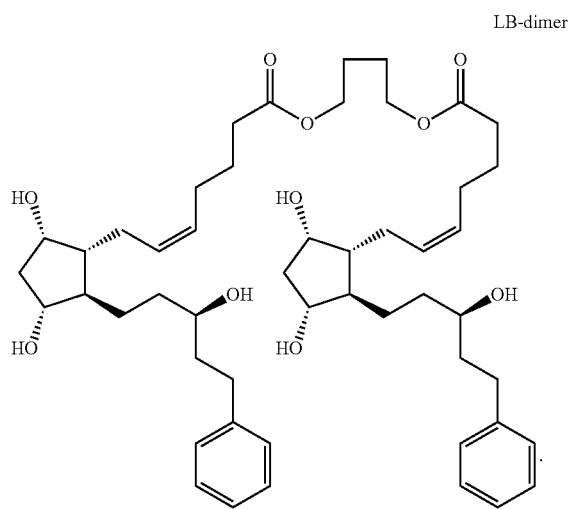 [SMILES: O=C(CCC/C=C\C[C@@H]1[C@@H](CC[C@@H](O)CCc2ccccc2)[C@H](O)C[C@@H]1O)OCCCCOC(=O)CCC/C=C\C[C@@H]1[C@@H](CC[C@@H](O)CCc2ccccc2)[C@H](O)C[C@@H]1O]

In another aspect, the present invention provides a crude latanoprostene bunod composition comprising Compound LB-dimer as defined above in an amount greater than 0.1% and less than 5%, 5,6-trans isomer of latanoprostene bunod in an amount greater than 0.1% and less than 3.5%, and less than 0.5% 15S-latanoprostene bunod, aside from residual solvents and 1,4-butanediol dinitrate.

In another aspect, the present invention provides a crude latanoprostene bunod composition comprising Compound LB-dimer as defined above in an amount greater than 0.1% and less than 5%, 5,6-trans isomer of latanoprostene bunod in an amount greater than 0.01% and less than 0.1%, and less than 0.1% 15S-latanoprostene bunod, aside from residual solvents and 1,4-butanediol dinitrate.

In another aspect, the present invention provides a purified latanoprostene bunod composition comprising Compound LB-dimer as defined above in an amount greater than 0% and less than 0.1%, 5,6-trans isomer of latanoprostene bunod in an amount greater than 0.1% and less than 3.5%, and less than 0.5% 15S-latanoprostene bunod.

In another aspect, the present invention provides a purified latanoprostene bunod composition comprising Compound LB-dimer as defined above in an amount greater than 0% and less than 0.1%, 5,6-trans isomer of latanoprostene bunod in an amount greater than 0.01% and less than 0.1%, and less than 0.1% 15S-latanoprostene bunod.

DETAILED DESCRIPTION OF THE INVENTION

Preparation of Latanoprost Acid

According to the present invention, a process for preparing latanoprostene bunod comprising reacting latanoprost acid with 1,4-butanoediol dinitrate is provided.

In some embodiments, the latanoprost acid may be prepared by any conventional methods. For example, the latanoprost acid can be prepared by a hydrolysis reaction of latanoprost or latanoprost 1,9-lactone as shown in Scheme 3:

Scheme 3

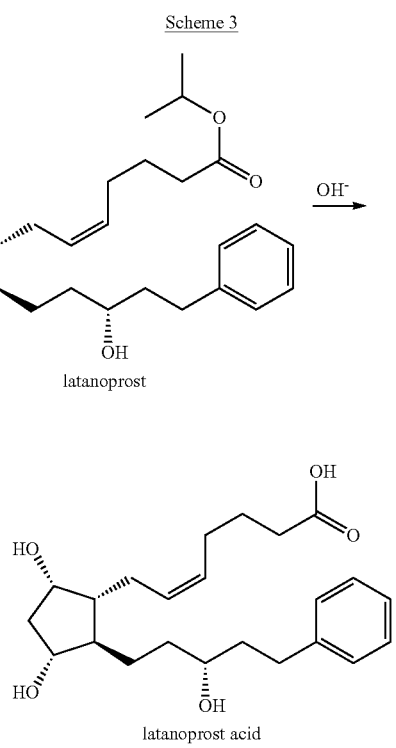

latanoprost latanoprost acid

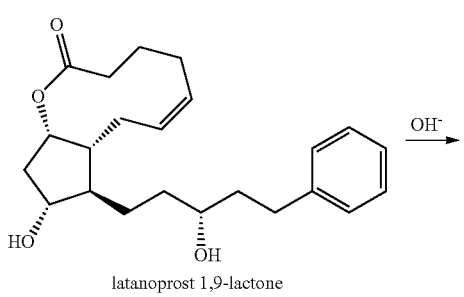

latanoprost 1,9-lactone

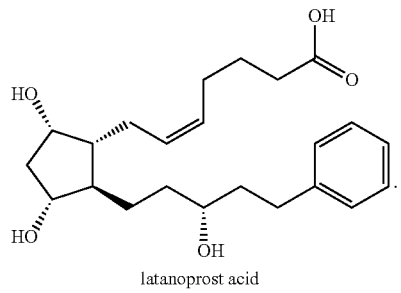

latanoprost acid

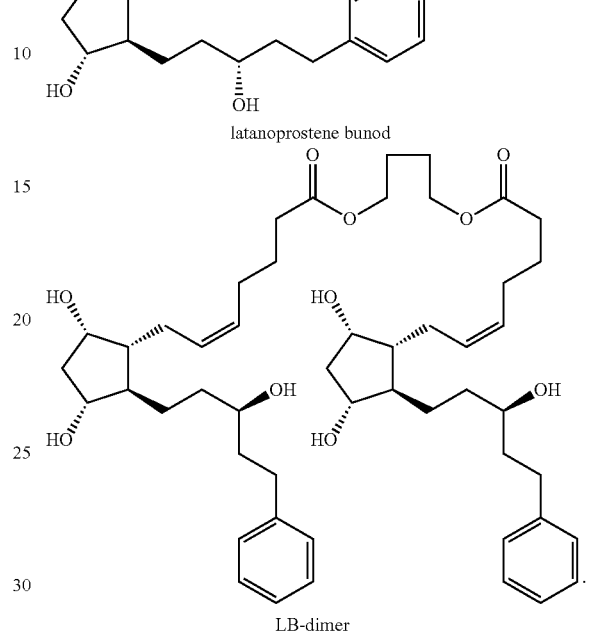

latanoprostene bunod

LB-dimer

In some embodiments, the hydrolysis reaction may be performed using sodium hydroxide, potassium hydroxide, lithium hydroxide monohydrate or the like, and it is particularly preferably performed using lithium hydroxide monohydrate. At this time, ethanol, methanol, isopropyl alcohol, water or a mixed solvent thereof may be used as a reaction solvent, and a mixed solvent of methanol and water is particularly preferable. In some embodiments, the reaction temperature is preferably room temperature, and the reaction time is preferably about 1 to 20 hours.

In some embodiments, the latanoprost acid can be prepared from latanoprost. Typically, commercially available latanoprosts that satisfy the USP requirements contain about 3.5% 5,6-trans isomer and about 0.5% 15S-isomer. Accordingly, latanoprost acids obtained from the commercially available latanoprosts by hydrolysis will also contain about 3.5% 5,6-trans isomer and about 0.5% 15S-isomer. The latanoprost acids thus prepared are denoted in the specification as latanoprost acid-A.

In some embodiments, the latanoprost acid can be prepared from latanoprost 1,9-lactone. In the present embodiment, latanoprost 1,9-lactone disclosed in U.S. Pat. No. 9,994,543 is used to prepare latanoprost acids through hydrolysis. The latanoprost acids thus prepared are substantially free of isomer and contain less than 0.1% 5,6-trans isomer and 0.1% 15S-isomer, and are denoted in the specification as latanoprost acid-B.

Preparation of Latanoprostene Bunod

According to the present invention, latanoprostene bunod is prepared by esterifying latanoprost acid with 1,4-butanediol dinitrate as shown in Scheme 4:

Scheme 4

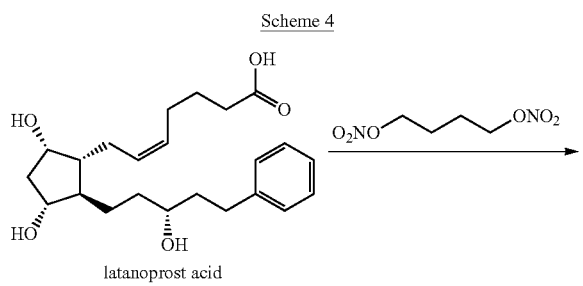

latanoprost acid

In some embodiments, the reaction can be carried out in the presence of a base. Examples of suitable bases include, but are not limited to, 1,5-diazabicyclo[4.3.0]non-5-ene (DBN), 1,8-diazabicyclo[5.4.0]undec-7-ene (DBU), sodium hydroxide, and potassium carbonate, and it is particularly preferable to use 1,5-diazabicyclo[4.3.0]non-5-ene (DBN), 1,8-diazabicyclo[5.4.0]undec-7-ene (DBU), or potassium carbonate.

In some embodiments, the reaction can be carried out in a solvent. Examples of suitable solvents include, but are not limited to, acetone, dichloromethane, toluene, tetrahydrofuran (THF), and dimethylformamide (DMF), and it is particularly preferable to perform the reaction using dimethylformamide.

In the present invention, the amount used of 1,4-butanediol dinitrate is not particularly limited. In some embodiments, 1,4-butanediol dinitrate may be used in an amount ranging from about 1 to 100 parts by weight, preferably about 3 to 30 parts by weight or about 5 to 15 parts by weight, and more preferably about 5 to 10 parts by weight per 1 part by weight of latanoprost acid.

In some embodiments, the reaction temperature is preferably about 20 to 80° C., about 20 to 70° C. ° C., about 20 to 60° C., about 20 to 50° C., about 20 to 40° C. or about 20 to 30° C. The reaction time varies depending on the reaction temperature and it is preferably about 1 to 6 hours, about 1 to 5 hours, about 1 to 4 hours, about 1 to 3 hours or about 1 to 2 hours.

As shown in Scheme 4, the process for preparing latanoprostene bunod further comprises forming a by-product of Formula LB-dimer.

In some embodiments, the use of latanoprost acid-A as the starting material in the present process can provide a crude latanoprostene bunod composition A comprising Compound LB-dimer in an amount greater than about 0.1% and less than about 5%, 5,6-trans isomer of latanoprostene bunod in an amount greater than about 0.1% and less than about 3.5%, and less than about 0.5% 15S-latanoprostene bunod, aside from residual solvents and 1,4-butanediol dinitrate. In some embodiments, 15S-latanoprostene bunod and 5,6-trans isomer of latanoprostene bunod are generated from 15S-isomer and 5,6-trans isomer, respectively, in the starting material of latanoprost acid-A. In some embodiments, the crude latanoprostene bunod composition A contains no Compound LB-Br or Compound LB-I.

In some embodiments, the use of latanoprost acid-B as the starting material in the present process can provide a crude latanoprostene bunod composition B, comprising Compound LB-dimer in an amount greater than about 0.1% and less than about 5%, 5,6-trans isomer of latanoprostene bunod in an amount greater than about 0.01% and less than about 0.1%, and less than about 0.1% 15S-latanoprostene bunod, aside from residual solvents and 1,4-butanediol dinitrate. In some embodiments, 15S-latanoprostene bunod and 5,6-trans isomer of latanoprostene bunod are generated from 15S-isomer and 5,6-trans isomer, respectively, in the starting material of latanoprost acid-B. In some embodiments, the crude latanoprostene bunod composition B contains no Compound LB-Br or Compound LB-1.

In the present processes, although the crude latanoprostene bunod compositions A and B each include an excess amount of the reaction reagent of 1,4-butanediol dinitrate (TLC ΔRf>0.7, 33% hexane in ethyl acetate) and the by-product, Compound LB-dimer (TLC ΔRf>0.5, 100% ethyl acetate), the excess amount of the reaction reagent and the by-product can be easily removed by typical or simple chromatography. However, in the prior art processes, such as those disclosed in WO 2005/068421, WO 2017/093771 and WO 2019/031774, impurities in which TLC ΔRf is less than 0.1, such as Compound LB-Br (TLC ΔRf<0.04, 33% hexane in ethyl acetate), Compound LB-I (TLC ΔRf<0.07, 33% hexane in ethyl acetate) and 5,6-trans isomer of latanoprostene bunod (TLC ΔRf<0.01, 33% hexane in ethyl acetate) would be generated, but cannot be easily removed by typical chromatography, and can only be removed via difficult or complicated chromatography. Accordingly, the present processes are simpler and more cost effective than the prior art processes.

In addition to the excess amount of the reaction reagent of 1,4-butanediol dinitrate and the by-product (Compound LB-dimer), the crude latanoprostene bunod further comprises a small amount of high-polarity non-prostaglandin impurities and low-polarity non-prostaglandin impurities that are generated from the reagents or solvents. In the present processes, the crude latanoprostene bunod can be purified using typical chromatography only one time, so that the excess amount of 1,4-butanediol dinitrate, Compound LB-dimer, high-polarity non-prostaglandin impurities and low-polarity non-prostaglandin impurities can simultaneously be removed.

In some embodiments, all of the hydroxyl groups of the crude latanoprostene bunod can be protected by silyl protecting groups for forming protected latanoprostene bunod with low-polarity. Then, the protected latanoprostene bunod with low-polarity can be optionally purified by typical chromatography to remove the high-polarity non-prostaglandin impurities. After that, the protected latanoprostene bunod is desilylated to form a crude latanoprostene bunod with high-polarity, which does not contain any high-polarity non-prostaglandin impurities. Then, the crude latanoprostene bunod with high-polarity can be further purified only once using typical chromatography to remove the low-polarity non-prostaglandin impurities.

The typical chromatography that is suitable for use in the present processes is known in the art and widely and commonly used. In the present processes, the typical chromatography can be used to purify the crude latanoprostene bunod or the crude protected latanoprostene bunod. For example, the column chromatography with cost-saving irregular silica gel having a common particle size of 63 to 200 μm or 50 to 150 μm can be used to efficiently remove the excess amount of the reaction reagent, the by-product and the non-prostaglandin impurities. Moreover, as long as the amount used of the silica gel is about (or more than) 3-fold the amount of the materials to be separated, the above impurities can be removed to less than about 0.1%. Preferably, the amount used of the silica gel is about 5- to 50-fold the amount of the materials to be separated. More preferably, the amount used of the silica gel is about 5- to 20-fold the amount of the materials to be separated.

In some embodiments, a bi-component mixture of apolar and polar solvents may be applied as an eluent in various compositions. Examples of the apolar solvents of the bi-component mixture include, but are not limited to, hydrocarbons, halogenated aliphatic hydrocarbons and ether-type solvents, such as pentane, hexane, heptane, cyclohexane, and dichloromethane and diisopropyl ether. Examples of the polar solvents of the bi-component mixture include, but are not limited to, alcohol-, ester- or ketone-type solvents containing straight- or branched-chain alkyl groups.

In some embodiments, the crude latanoprost bunod can be purified via silylation and desilylation. In some embodiments, the crude latanoprostene bunod may be purified by silylating all the hydroxyl groups in the latanoprostene bunod with a silylating agent comprising the residue —SiR$_a$R$_b$R$_c$ to form a crude compound of Formula LB-3Si:

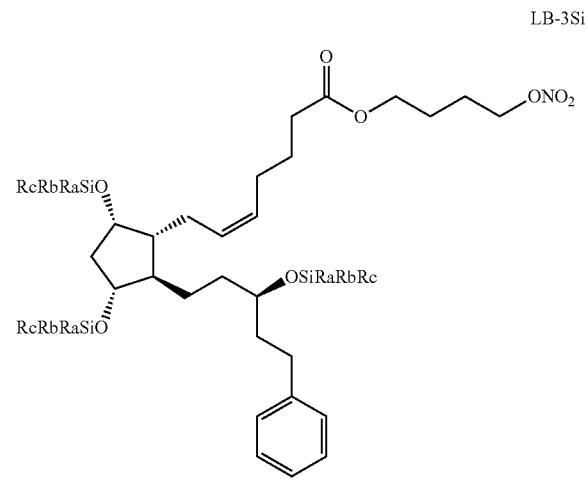

wherein R$_a$, R$_b$ and R$_c$ are each independently C$_{1-8}$ alkyl, phenyl, benzyl, a substituted phenyl, or a substituted benzyl. In some embodiments, the silylating agent has a formula of XSiR$_a$R$_b$R$_c$ wherein X is a halogen, such as F, Cl, or Br; and R$_a$, R$_b$ and R$_c$ are each independently a C$_{1-8}$ alkyl, phenyl, benzyl, a substituted phenyl, or a substituted benzyl. According to an embodiment of the present invention, the silylating agent suitable for the purification reaction is selected from the group consisting of trimethylsilyl chloride, triethylsilyl chloride, dimethyl(octyl)silyl chloride, and tert-butyldimethylsilyl chloride.

In some embodiments, the crude compound of Formula LB-3Si can be purified by typical chromatography. Since the compound of Formula LB-3Si has very low polarity, impurities with higher polarity, for example, the impurities generated from the solvents such as DMF and from the reagents such as 1,4-butanediol dinitrate, can be easily removed by using simple chromatography. The resultant compound of Formula LB-3Si is then desilylated, to form another crude latanoprostene bunod. Then, the another crude latanoprostene bunod can be purified by typical chromatography to form latanoprostene bunod having an improved purity. In some embodiments, the conditions for carrying out the silylation and desilylation reactions are those obvious to persons skilled in the art.

In some embodiments, the purification of the crude compound of Formula LB-3Si can be optionally performed. In the present processes, the impurities with higher polarity can be decreased to less than 0.1% for meeting the regulatory requirements even when merely purifying the crude latanoprostene bunod using typical chromatography, i.e., without the purification of the compound of Formula LB-3Si. In some embodiments, the impurities with higher polarity can be decreased to less than 0.1%, or less than the detection limit of high-performance liquid chromatography (HPLC), by the additional purification of the compound of Formula LB-3Si using typical chromatography.

In some embodiments, a purified latanoprostene bunod composition C by using latanoprost acid-A as a starting material comprising Compound LB-dimer in an amount greater than about 0% and less than about 0.1%, 5,6-tram isomer of latanoprostene bunod in an amount greater than about 0.1% and less than about 3.5%, and less than about 0.5% 15S-latanoprostene bunod is obtained. In some embodiments, the purified latanoprostene bunod composition C is obtained by purifying the crude latanoprostene bunod composition A. In some embodiments, the purified latanoprostene bunod composition C contains no Compound LB-Br or Compound LB-I.

In some embodiments, a purified latanoprostene bunod composition D by using latanoprost acid-B as a starting material comprising Compound LB-dimer in an amount greater than 0% and less than 0.1%, 5,6-trans isomer of latanoprostene bunod in an amount greater than 0.01% and less than 0.1%, and less than 0.1% 15S-latanoprostene bunod is obtained. In some embodiments, the purified latanoprostene bunod composition D is obtained by purifying the crude latanoprostene bunod composition B. In some embodiments, the purified latanoprostene bunod composition D contains no Compound LB-Br or Compound LB-I.

It will be understood that particular embodiments described herein are shown by way of illustration and not as limitations of the invention. The principal features of this invention can be employed in various embodiments without departing from the scope of the invention. Those skilled in the art will recognize or be able to ascertain, using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but is also consistent with the meaning of "one or more," "at least one," and "one or more than one." The use of the term "or" in the claims is used to mean "and/or" unless explicitly indicated to refer to alternatives only or unless the alternatives are mutually exclusive, although the disclosure supports a definition that refers only to alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, persons skilled in the art will appreciate that many such ratios, ranges, and ranges of ratios can be unambiguously derived from the numerical values presented herein and in all instances such ratios, ranges, and ranges of ratios represent various embodiments of the present invention.

All of the compounds and/or methods disclosed and claimed herein can be made and executed without undue experimentation in light of the present disclosure. While the compounds and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutions and modifications apparent to those skilled in the art are deemed to be within the spirit, scope and concept of the invention as defined by the appended claims.

EXAMPLES

Example 1

Preparation of Latanoprost Acid-A

A solution of latanoprost (containing 2.38% 5,6-trans isomer and 0.05% 15S-isomer) (1.0 g, 2.31 mmol) in isopropyl alcohol (8 mL) was treated with 3N potassium hydroxide aqueous solution (3.85 mL). The mixture was stirred at 50 to 55° C. for 2 hours, cooled, and then adjusted to pH of 8.0 to 8.3 with 3N hydrochloric acid aqueous solution. Then, most of the solvent was removed under reduced pressure. The residue was diluted with a saturated aqueous solution of sodium bicarbonate (5 mL) and ethyl acetate (2 mL). The mixture was then stirred at room temperatures for 5 minutes, and the organic phase and the aqueous phase were separately collected. The aqueous layer was adjusted to pH of 3.0 to 3.2 with 3N hydrochloric acid aqueous solution at room temperature and extracted with ethyl acetate (20 mL). The organic layer was dried over magnesium sulfate (3 g) and concentrated under reduced pressure to give 1.1 g of crude latanoprost acid-A. HPLC analysis of the product showed that it contains 2.34% 5,6-trans isomer and 0.05% 15S-isomer.

Example 2

Preparation of Latanoprost Acid-B

A solution of latanoprost 1,9-lactone obtained by the method disclosed in U.S. Pat. No. 9,994,543 (30.0 g, 0.08 mol) in isopropyl alcohol (240 mL) was treated with 3N potassium hydroxide aqueous solution (100 mL). The mixture was stirred at 50 to 55° C. for 2 hours, cooled, and then adjusted to pH of 8.0 to 8.3 with 3N hydrochloric acid aqueous solution. Then, most of the solvent was removed under reduced pressure. The residue was diluted with a saturated aqueous solution of sodium bicarbonate (150 mL) and ethyl acetate (60 mL). The mixture was then stirred at room temperature for 5 minutes, and the organic phase and the aqueous phase were separately collected. The aqueous layer was adjusted to pH of 3.0 to 3.2 with 3N hydrochloric acid aqueous solution at room temperature and extracted with ethyl acetate (500 mL). The organic layer was dried over magnesium sulfate (60 g) and concentrated under reduced pressure to give 36.2 g of crude latanoprost acid-B. HPLC analysis of the product showed that no isomer was detectable.

$^1$H-NMR (400 MHz, CDCl$_3$):δ 7.253-7.282 (m, 2H), 7.157-7.194 (m, 3H), 5.455-5.506 (m, 1H), 5.342-5.394 (m, 1H), 4.142-4.152 (m, 1H), 3.936 (m, 1H), 3.664-3.711 (m, 1H), 2.754-2.813 (m, 1H), 2.618-2.678 (m, 1H), 2.327 (t, 2H), 2.241 (t, 2H), 2.133 (q, 2H), 1.496-1.892 (m, 10H), 1.307-1.382 (m, 2H)

$^{13}$C-NMR (100 MHz, CDCl$_3$):δ 177.395, 142.122, 129.454, 129.416, 128.392, 128.376, 125.788, 78.386, 74.234, 71.509, 52.139, 51.433, 42.461, 38.749, 35.228, 33.201, 32.070, 29.049, 26.575, 26.408, 24.662

Comparative Example 3

Synthesis of Latanoprostene bunod by Latanoprost acid-B with 4-bromobutyl nitrate A solution of crude latanoprost acid-B (213 mg, 0.54 mmol) in DMF (5 mL) was treated with K$_2$CO$_3$ (206 mg, 1.49 mmol), KI (77 mg, 0.46 mmol) and 4-bromobutyl nitrate (805 mg, 25% w/w in methylene chloride, 1.02 mmol). The mixture was then stirred at 45 to 50° C. for 2 hours under an atmosphere of nitrogen (TLC monitoring). The mixture was diluted with ethyl acetate (100 mL), washed with brine (2×50 mL), dried over magnesium sulfate and concentrated under reduced pressure to give 0.43 g of crude Latanoprostene bunod. HPLC analysis of the crude Latanoprostene bunod showed that it contained 4.59% compound LB-Br, and 0.91% compound LB-1, and no 5,6-trans Latanoprostene bunod and 15S-Latanoprostene bunod were detected Latanoprostene Bunod:

TLC: Rf 0.205 (33% hexane in ethyl acetate); Rf 0.705 (100% ethyl acetate)

$^1$H-NMR (400 MHz, CDCl$_3$):δ 7.245-7.281 (m, 2H), 7.146-7.192 (m, 3H), 5.445-5.490 (m, 1H), 5.331-5.427 (m, 1H), 4.451 (t, 2H), 4.130 (m, 1H), 4.078 (t, 2H), 3.927 (m, 1H), 3.637 (m, 1H), 3.073 (s, 1H), 2.613-2.781 (m, 3H), 2.263-2.341 (m, 3H), 2.027-2.208 (m, 4H), 1.495-1.862 (m, 14H), 1.294-1.391 (m, 2H)

$^{13}$C-NMR (100 MHz, CDCl$_3$):δ 173.877, 142.113, 129.514, 129.331, 128.390, 125.810, 78.676, 74.592, 72.619, 71.298, 63.473, 52.733, 51.799, 42.494, 39.025, 35.762, 33.583, 32.103, 29.583, 26.889, 26.600, 24.938, 24.824, 23.617

Compound LB-Br:

TLC: Rf 0.239 (33% hexane in ethyl acetate)

$^1$H-NMR (400 MHz, CDCl$_3$):δ 7.162-7.298 (m, 5H), 5.351-5.478 (m, 2H), 4.158 (m, 1H), 4.091 (t, 2H), 3.946 (m, 1H), 3.664 (m, 1H), 3.422 (t, 2H), 2.634-2.829 (m, 3H), 2.299-2.361 (m, 4H), 2.091-2.227 (m, 3H), 1.510-2.227 (m, 15H), 1.252-1.419 (m, 2H)

$^{13}$C-NMR (100 MHz, CDCl$_3$):δ 173.877, 142.052, 129.468, 129.430, 128.413, 128.390, 125.832, 78.797, 74.744, 71.313, 63.442, 52.907, 51.883, 42.532, 39.063, 35.784, 33.614, 33.052, 32.111, 29.629, 29.287, 27.299, 26.942, 26.631, 24.839

Compound LB-4:

TLC: Rf 0.273 (33% hexane in ethyl acetate)

$^1$H-NMR (400 MHz, CDCl$_3$):δ 7.150-7.286 (m, 5H), 5.355-5.474 (m, 2H), 4.136 (m, 1H), 4.069 (t, 2H), 3.930 (m, 1H), 3.644-3.661 (m, 1H), 3.185 (t, 2H), 2.619-2.805 (m, 3H), 2.268-2.324 (m, 3H), 2.808-2.214 (m, 4H), 1.501-1.910 (m, 15H), 1.350-1.373 (m, 2H)

$^{13}$C-NMR (100 MHz, CDCl$_3$):δ 173.915, 142.105, 129.476, 129.400, 128.398, 125.810, 78.691, 74.592, 71.298, 63.237, 52.756, 51.814, 42.532, 39.033, 35.762, 33.636, 32.118, 29.986, 29.583, 29.538, 26.889, 26.623, 24.847, 5.918

Comparative Example 4

Synthesis of Latanoprostene Bunod by Compound LB-Br with Silver Nitrate

Compound LB-Br (0.5 g, 0.95 mmol) was dissolved in acetonitrile (7.5 mL), silver nitrate (0.29 g, 1.71 mmol) was added, and then the mixture was heated and stirred at about 35 to 40° C. for about 55 hours. The progress of the reaction was observed by HPLC and shown in Table 1.

TABLE 1

| Compound (Relative Retention Time) | LB-Br (0.79) | Latanoprostene bunod (1.00) | 5,6-trans Latanoprostene bunod (1.14) | Other impurities |
|---|---|---|---|---|
| 1 hr. | 76.45% | 23.36% | ND | 0.19% |
| 2 hr. | 65.97% | 33.76% | ND | 0.27% |
| 3 hr. | 56.29% | 43.48% | ND | 0.23% |
| 4 hr. | 45.95% | 53.76% | ND | 0.28% |
| 6 hr. | 36.20% | 63.32% | ND | 0.48% |
| 24 hr. | 3.34% | 95.71% | 0.25% | 0.60% |
| 27 hr. | 2.31% | 96.81% | 0.28% | 0.60% |
| 30 hr. | 1.55% | 97.48% | 0.38% | 0.58% |
| 48 hr. | 0.59% | 98.23% | 0.60% | 0.59% |
| 52 hr. | 0.43% | 98.27% | 0.72% | 0.58% |
| 55 hr. | 0.35% | 98.30% | 0.77% | 0.58% |

As shown in Table 1, after 55 hours of the reaction, there is still 0.35% Compound LB-Br unreacted, but 0.77% 5,6-trans latanoprostene bunod has been generated from isomerization of latanoprostene bunod. Since 5,6-trans latanoprostene bunod is more difficult to be removed than Compound LB-Br by chromatograph, continuing the reaction will not increase the yield but only raise the cost of purification.

Example 5

Synthesis of Latanoprostene Bunod by Latanoprost Acid-A with 1,4-Butanediol Dinitrate A solution of crude Latanoprost acid-A (5-trans isomer>2%) (1.1 g, 2.82 mmol) in DMF (6 mL) was treated with $K_2CO_3$ (1.17 g, 8.47 mmol) and 1,4-butanediol dinitrate (7.61 g, 42.25 mmol). The mixture was then stirred at 60 to 65° C. for 2.5 hours under an atmosphere of nitrogen (TLC monitoring), and then cooled to room temperature. The reaction mixture was diluted with ethyl acetate (20 mL), washed with ice water (2×15 mL), dried over magnesium sulfate (3 g) and concentrated under reduced pressure to give 9.8 g of crude Latanoprostene bunod and excess 1,4-butanediol dinitrate. HPLC analysis of the crude Latanoprostene bunod composition showed that it comprises 1.4% compound LB-dimer, 2.38% 5,6-trans isomer of latanoprostene bunod, and 0.05% 15S-latanoprostene bunod, aside from residual solvents and 1,4-butanediol dinitrate. The excess 1,4-butanediol dinitrate and Compound LB-dimer were removed by column chromatography with 5-fold amount of silica gel, and then concentrated under reduced pressure to provide 1.2 g of purified Latanoprostene bunod (83.9% yield). HPLC analysis of the purified Latanoprostene bunod composition showed that it comprises 0.001% Compound LB-dimer, 2.4% 5,6-trans isomer of latanoprostene bunod, and 0.06% 15S-latanoprostene bunod.

Latanoprostene Bunod:

TLC: Rf 0.205 (33% hexane in ethyl acetate); Rf 0.705 (100% ethyl acetate)

$^1$H-NMR (400 MHz, CDCl$_3$):δ 7.245-7.282 (m, 2H), 7.146-7.192 (m, 3H), 5.446-5.491 (m, 1H), 5.331-5.427 (m, 1H), 4.452 (t, 2H), 4.130 (m, 1H), 4.079 (t, 2H), 3.927 (m, 1H), 3.639 (m, 1H), 3.042 (s, 1H), 2.610-2.801 (m, 3H), 2.264-2.343 (m, 3H), 2.059-2.209 (m, 4H), 1.495-1.863 (m, 14H), 1.294-1.393 (m, 2H)

$^{13}$C-NMR (100 MHz, CDCl$_3$):δ 173.870, 142.113, 129.514, 129.331, 128.390, 125.810, 78.683, 74.600, 72.619, 71.298, 63.465, 52.740, 51.807, 42.501, 39.025, 35.762, 33.583, 32.103, 29.583, 26.889, 26.600, 24.938, 24.824, 23.625

Compound LB-Dimer:

TLC: Rf 0.0 (33% hexane in ethyl acetate): Rf 0.193 (100% ethyl acetate)

$^1$H-NMR (400 MHz, CDCl$_3$):δ 7.240-7.277 (m, 2H), 7.142-7.190 (m, 3H), 5.421-5.483 (m, 1H), 5.325-5.387 (m, 11H), 4.068-4.117 (m, 3H), 3.919 (m, 1H), 3.604-3.663 (m, 1H), 2.611-2.816 (m, 3H), 2.264-2.342 (m, 4H), 2.030-2.210 (m, 4H), 1.465-1.902 (m, 12H), 1.228-1.381 (m, 2H)

$^{13}$C-NMR (100 MHz, CDCl$_3$):δ 174.014, 142.151, 129.536, 129.347, 128.390, 125.787, 78.622, 74.463, 71.268, 63.921, 52.649, 51.739, 42.524, 39.010, 35.739, 33.629, 32.118, 29.538, 26.858, 26.593, 25.272, 24.839

Example 6

Synthesis of Latanoprostene Bunod by Latanoprost Acid-B with 1,4-Butanediol Dinitrate A solution of crude Latanoprost acid-B (35.00 g, 0.09 mol) in DMF (175 mL) was treated with $K_2CO_3$ (37.16 g, 0.27 mol) and 1,4-butanediol dinitrate (242.15 g, 1.34 mol). The mixture was then stirred at 60 to 65° C. for 2.5 hours under an atmosphere of nitrogen (TLC monitoring) and then cooled to room temperature. The reaction mixture was diluted with ethyl acetate (600 mL), washed with ice water (2×530 mL), dried over magnesium sulfate (30 g) and concentrated under reduced pressure to give 268 g crude latanoprostene bunod and excess 1,4-butanediol dinitrate. HPLC analysis of the crude latanoprostene bunod composition showed that it comprises 1.4% Compound LB-dimer and 0.02% 5,6-trans isomer of latanoprostene bunod, and no 15S-latanoprostene bunod was detected, aside from residual solvents and 1,4-butanediol dinitrate. The excess 1,4-butanediol dinitrate and Compound LB-dimer were removed by column chromatography with 5-fold amount of silica gel, and then concentrated under reduced pressure to provide 40.94 g of purified Latanoprostene bunod (90.0% yield). HPLC analysis of the purified latanoprostene bunod composition showed that it comprises 0.0003% compound LB-dimer and 0.03% 5,6-trans isomer of latanoprostene bunod, and no 15S-latanoprostene bunod was detected. Purity: >99.90%.

Example 7

Synthesis of Latanoprostene Bunod by Latanoprost Acid-B with 1,4-Butanediol Dinitrate Via Latanoprostene Bunod-3TES A solution of crude Latanoprost acid-B (30.0 g, 76.8 mmol) in DMF (150 mL) was treated with $K_2CO_3$ (31.85 g, 0.23 mol) and 1,4-butanediol dinitrate (207 g). The mixture was then stirred at 60 to 65° C. for 2.5 hours under an atmosphere of nitrogen (TLC monitoring). The reaction mixture was cooled to room temperature. The reaction mixture was diluted with ethyl acetate (500 mL), washed with ice water (2×500 mL), dried over magnesium sulfate and concentrated under reduced pressure to give a crude Latanoprostene bunod. Triethylsilyl chloride (47.60 g, 0.32 mol) was added to a solution of the crude latanoprostene bunod and imidazole (26.83 g, 0.39 mol) in ethyl acetate (400 mL) at room temperature and the mixture was stirred for 0.5 hours (TLC monitoring). A saturated aqueous solution of sodium bicarbonate (200 mL) was poured into the reaction mixture, and the mixture was stirred for 5 minutes. The organic layer was separated and extracted with a saturated aqueous solution of sodium bicarbonate. The organic layer was dried over magnesium sulfate, solids were filtered off, and the filtrate was concentrated under reduced pressure to give the crude compound LB-3Si. The crude compound LB-3Si was purified by column chromatography to provide 65.2 g of Compound LB-3Si.

Compound LB-3Si:

(Z)-4-(nitrooxy)butyl 7-((1R,2R,3R,5S)-2-((R)-5-phenyl-3-((triethylsilyl)oxy)pentyl)-3,5-bis((triethylsilyl)oxy)cyclopentyl)hept-5-enoate $^1$H-NMR (400 MHz, CDCl$_3$):δ 7.250-7.286 (m, 2H), 7.147-7.181 (m, 3H), 5.422-5.484 (m, 1H), 5.308-5.371 (m, 1H), 4.457 (t, 2H), 4.069-4.108 (m, 3H) 3.665-3.758 (m, 2H), 2.566-2.718 (m, 2H), 2.224-2.314 (m, 3H), 2.061-2.183 (m, 4H), 1.745-1.822 (m, 8H), 1.590-1.697 (m, 2H), 1.458-1.520 (m, 2H), 1.254-1.412 (m, 3H), 0.930-0.987 (m, 27H), 0.535-0.634 (m, 18H)

$^{13}$C-NMR (100 MHz, CDCl$_3$):δ 173.566, 142.675, 130.295, 128.739, 128.299, 128.269, 125.620, 76.186, 72.566, 72.338, 71.746, 63.199, 50.281, 48.103, 44.194, 39.124, 34.471, 33.743, 31.716, 28.065, 26.722, 25.864, 24.991, 24.931, 23.625, 6.988, 6.881, 6.866, 5.166, 4.954, 4.923\ p-toluenesulfonic acid monohydrate (1 g) was added to a stirred solution of Compound LB-3Si in methanol (250 mL). The mixture was stirred for 2 hours at room temperature (TLC monitoring). Then, the reaction mixture was quenched with a saturated sodium bicarbonate aqueous solution, and the methanol was removed under reduced pressure. The residue was extracted with ethyl acetate. The organic layer was separated. The aqueous layer was extracted with ethyl acetate. The combined organic layer was dried over magnesium sulfate, filtered and concentrated under reduced pressure to give the crude latanoprostene bunod. HPLC (Phenomenex Luna 5 μm silica) analysis of the crude latanoprostene bunod composition showed that it comprises 0.8% Compound LB-dimer and 0.02% 5,6-trans isomer of latanoprostene bunod, and no 15S-latanoprostene bunod was detected. The crude product was subjected to further purification by flash column chromatography to obtain 34.8 g of the product. HPLC analysis of the purified Latanoprostene bunod composition showed that it comprises 0.0001% Compound LB-dimer and 0.02% 5,6-trans isomer of latanoprostene bunod, and no 15S-latanoprostene bunod was detected. Purity: >99.95%.

What is claimed is:

1. A process for preparing latanoprostene bunod comprising reacting latanoprost acid with 1,4-butanediol dinitrate.

2. The process according to claim 1 further comprising purifying the latanoprostene bunod by:
   silylating all the hydroxyl groups in the latanoprostene bunod with a silylating agent comprising the residue —SiR$_a$R$_b$R$_c$ to form a compound of Formula LB-3Si

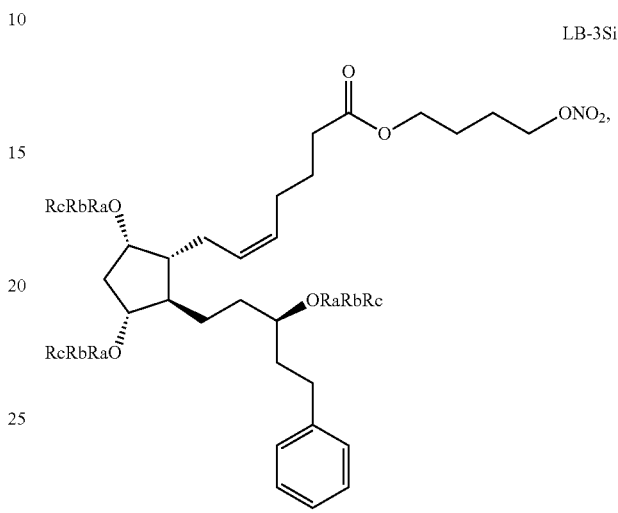

LB-3Si wherein R$_a$, R$_b$ and R$_c$ are each independently C$_{1-8}$ alkyl, phenyl, benzyl, a substituted phenyl, or a substituted benzyl; and
   desilylating the compound of Formula LB-3Si.

3. The process according to claim 1, wherein the process also produces a compound of Formula LB-dimer,

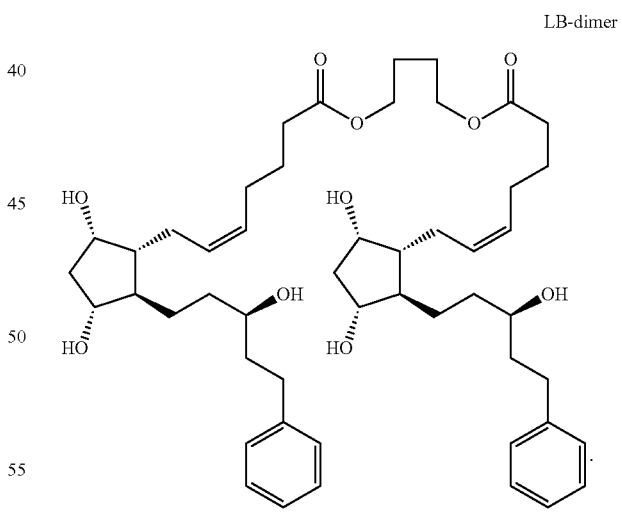

LB-dimer

* * * * *